(12) United States Patent
Gammons

(10) Patent No.: US 8,979,777 B2
(45) Date of Patent: Mar. 17, 2015

(54) PORTABLE COOL THERAPY DEVICE

(75) Inventor: Scott Gammons, Loudon, TN (US)

(73) Assignee: Adroit Medical Systems, Inc., Loudon, TN (US)

( * ) Notice: Subject to any disclaimer, the term of this patent is extended or adjusted under 35 U.S.C. 154(b) by 721 days.

(21) Appl. No.: 13/279,937

(22) Filed: Oct. 24, 2011

(65) Prior Publication Data
US 2012/0041347 A1 Feb. 16, 2012

Related U.S. Application Data

(63) Continuation-in-part of application No. 12/605,650, filed on Oct. 26, 2009, now Pat. No. 8,512,263.

(51) Int. Cl.
A61F 7/00 (2006.01)
A61F 7/02 (2006.01)

(52) U.S. Cl.
CPC . *A61F 7/02* (2013.01); *A61F 7/007* (2013.01); *A61F 7/0085* (2013.01); *A61F 2007/0054* (2013.01)
USPC .................. 601/15; 607/96; 607/104; 62/459

(58) Field of Classification Search
CPC ............... A61F 7/00; A61F 7/02; A61F 7/08; A61F 7/007; A61F 7/085; A61F 7/0053; A61F 2007/0054; A61F 2007/0056; A61F 2007/0069
USPC ........... 607/81, 85, 86, 87, 96, 104, 108, 109, 607/110, 111, 112, 114; 220/592.2, 592.23, 220/592.25; 206/523, 702, 728; 601/15; 62/459
See application file for complete search history.

(56) References Cited

U.S. PATENT DOCUMENTS

| | | | |
|---|---|---|---|
| 2,611,851 A | 9/1952 | Lott | |
| 2,828,903 A | 4/1958 | Adkins | |
| 2,839,654 A | 6/1958 | Jones et al. | |
| 3,536,248 A | 10/1970 | Malmo | |
| 3,627,116 A * | 12/1971 | Cooper | 206/497 |
| 4,320,856 A | 3/1982 | Stewart et al. | |
| 4,844,072 A | 7/1989 | French et al. | |
| 5,057,282 A | 10/1991 | Linder | |
| 5,062,527 A | 11/1991 | Westerman | |
| 5,245,221 A | 9/1993 | Schmidt et al. | |
| D345,802 S | 4/1994 | Mason et al. | |

(Continued)

OTHER PUBLICATIONS

International Search Report and Written Opinion for PCT/US2010/053912, dated Dec. 22, 2010, 19 pages.

*Primary Examiner* — Quang D Thanh
(74) *Attorney, Agent, or Firm* — Knox Patents; Thomas A. Kulaga

(57) ABSTRACT

Apparatus for a disposable, portable thermal therapy device that is self-contained for shipping as a single unit to a patient. The therapy device has a shipping configuration that presents a single, self-contained durable container. The container includes an insert that defines a compartment between the insert and the container. The compartment stores various electrical components, such as the power connection. The insert has a cavity that contains a pump and stores a thermal pad and associated fluid lines. The insert is a shell with a cable grip that secures the cable from pump and a recessed area for securing the pump. The edges of the insert are sealed to the inside surface of the box. A carrying strap is secured to the sidewalls of the box in a manner that prevents protrusions and aid in minimizing storage.

20 Claims, 9 Drawing Sheets

(56) References Cited

U.S. PATENT DOCUMENTS

| | | |
|---|---|---|
| 5,330,519 A | 7/1994 | Mason et al. |
| 5,336,249 A | 8/1994 | Mahawili |
| 5,476,489 A | 12/1995 | Koewler |
| 5,486,207 A | 1/1996 | Mahawili |
| 5,647,051 A | 7/1997 | Neer |
| 5,806,335 A | 9/1998 | Herbert et al. |
| 5,865,841 A | 2/1999 | Kolen et al. |
| 5,895,418 A | 4/1999 | Saringer |
| 5,948,012 A | 9/1999 | Mahaffey et al. |
| 6,086,609 A | 7/2000 | Buckley |
| 6,176,869 B1 | 1/2001 | Mason et al. |
| 6,551,348 B1 | 4/2003 | Blalock et al. |
| 3,736,309 A1 | 5/2004 | Westerman et al. |
| 6,837,420 B2 | 1/2005 | Westerman et al. |
| 6,962,600 B2 | 11/2005 | Lennox et al. |
| 7,052,509 B2 | 5/2006 | Lennox et al. |
| 7,347,327 B2 | 3/2008 | Lobman et al. |
| 2007/0187416 A1 * | 8/2007 | Maxson ............... 220/592.26 |
| 2008/0060374 A1 | 3/2008 | Gammons |

* cited by examiner

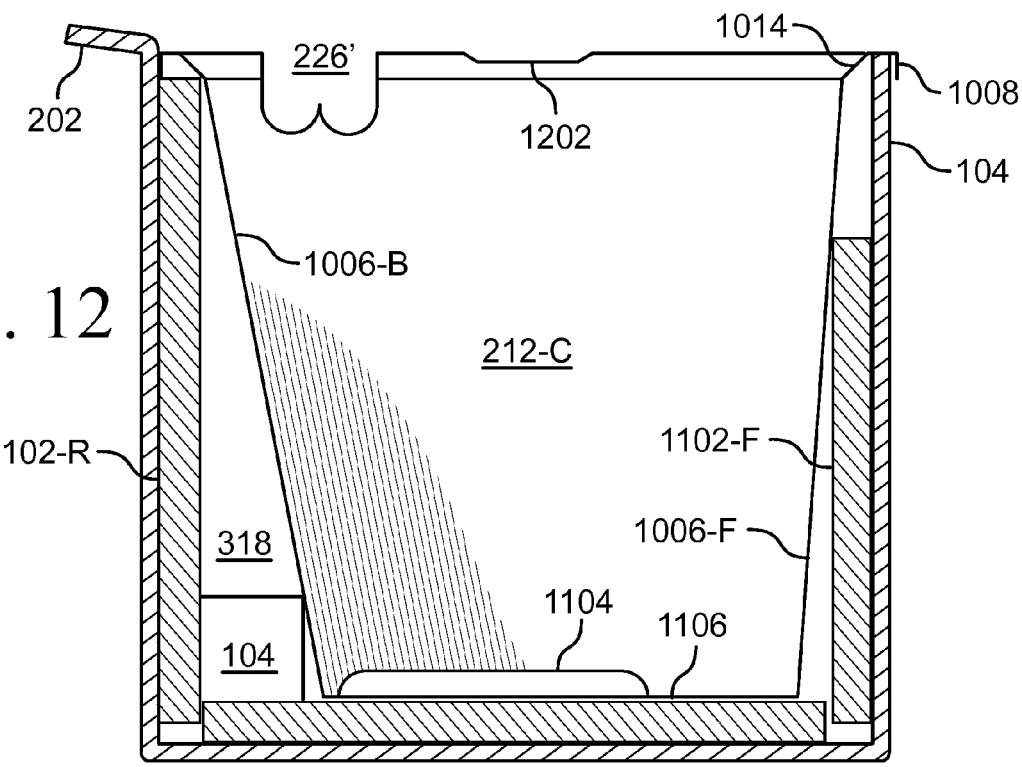
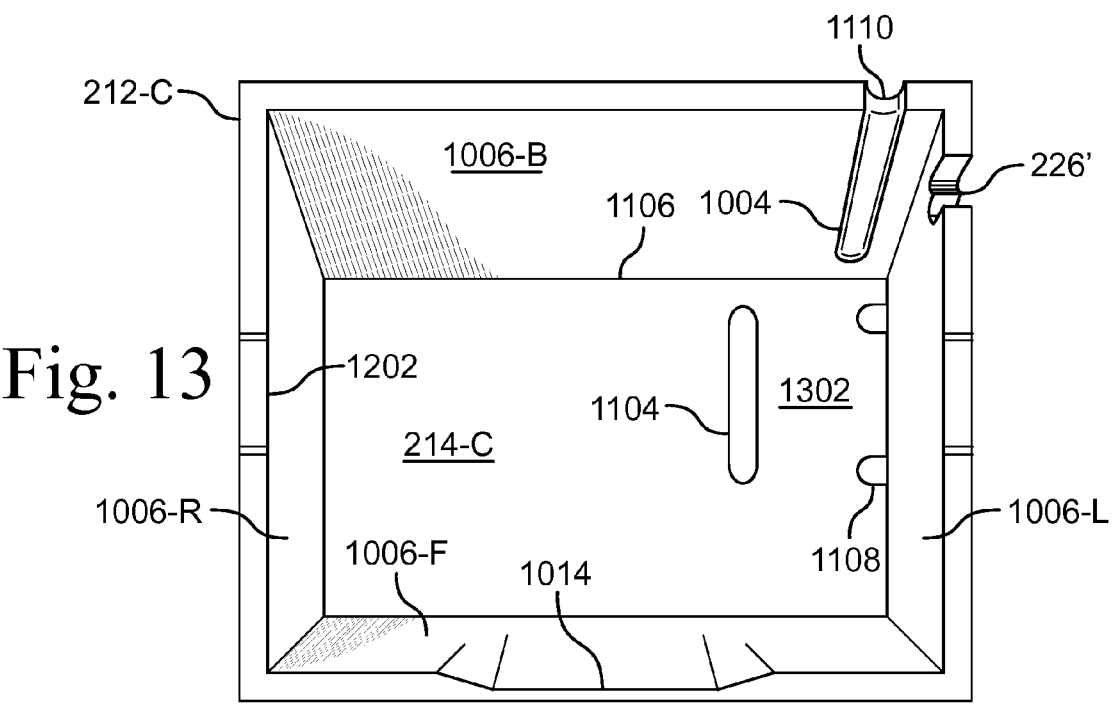

PORTABLE COOL THERAPY DEVICE

CROSS-REFERENCE TO RELATED APPLICATIONS

This application is a continuation-in-part of prior U.S. application Ser. No. 12/605,650, filed Oct. 26, 2009. This application claims the right of priority of PCT Application Number PCT/US2010/053912, filed Oct. 25, 2010, hereby incorporated by reference, which claims the benefit of U.S. application Ser. No. 12/605,650, filed Oct. 26, 2009.

STATEMENT REGARDING FEDERALLY SPONSORED RESEARCH OR DEVELOPMENT

Not Applicable

BACKGROUND OF THE INVENTION

1. Field of Invention

This invention pertains to a portable thermal therapy system that is disposable. More particularly, this invention pertains to a coolant system for temperature therapy of an animal in which the cooling system is self-contained for shipping and delivery and is adapted for single use.

2. Description of the Related Art

It is advantageous to selectively apply thermal treatment to patients. Hypothermic treatment is useful for emergency treatment of injured persons. A common first aid for sports injuries is to apply ice or cooling to the injured area. Additionally, patients are often prescribed treatment programs involving application of a thermal device to a body portion of the patient periodically over a period extending from days to months. Cooling treatment is also useful for providing comfort. Many menopausal women have found relief from hot flashes by using cooling treatment to quickly lower their body temperature during the onset of a hot flash.

Physicians have used various devices and techniques to cool the body, including pharmacological cooling and various types of mechanically induced cooling. Mechanically induced cooling approaches generally fall into one of three categories: conductive, convective, or evaporative. While different implementations have been tried, many are limited by lack of practicality, difficulty of use, ineffectiveness, and/or excessive power consumption.

Conductive cooling therapy, that is, a cooling treatment in which the heat transfer mechanism is conduction as opposed to radiation or convection, is known and has been used. Ice packs, although primitive, provide quick localized cooling. A disadvantage of ice packs is that it is difficult to control the rate of cooling. It is also known to circulate a cooled fluid through a thermal pad wrapped around an extremity of a person. The fluid is cooled using various techniques, including using a refrigerant to cool the fluid.

A variety of conductive cooling therapy devices are known. An example of one such device is disclosed in U.S. Pat. No. 7,640,764, issued Jan. 5, 2010, titled "Portable coolant system." The portable coolant system includes a hardshell cooler, such as a portable ice chest, with exposed fluid connectors. The configuration of the cooler is such that the cooler and peripheral components must be packaged in another container for shipping and handling in order to avoid damaging the various components and/or the exposed fluid connectors. Further, the hardshell ice chest is made of materials that are intended for extended use and it is not practical and economical to dispose of the portable coolant system after a patient completes a course of therapy.

These types of conductive cooling therapy devices are constructed for durability and are not suited for environmentally friendly disposal. Further, durable devices require components and construction techniques that make the therapy devices expensive, thereby discouraging the disposal of the therapy devices after the course of treatment is completed.

Foldable portable coolers are known. For example, U.S. Pat. No. 6,837,420, titled "Foldable portable cooler with enhanced over-center locking handle," issued on Jan. 4, 2005, discloses a container configured for storing beverage containers. Such foldable portable coolers are passive devices that provide advantages by being shipped and stored as flat blanks in bulk and being conveniently deployed by end users.

BRIEF SUMMARY OF THE INVENTION

According to one embodiment of the present invention, a portable thermal therapy device is provided. The therapy device has a shipping configuration in which the therapy device is self-contained in a lightweight, yet durable container that is suitable for shipping, handling, and storing. After being received by an end user, the therapy device has a deployed configuration in which various components are removed and/or extended from inside the container such that the therapy device is able to be used for treatment of a patient. In this way, the patient conveniently receives a single, preassembled therapy device requiring minimal assembly and setup.

The container includes a box and a lid, with an insert inside the box. The insert has a cavity that is insulated from the environment outside the box. Inside the cavity is a pump that is attached to the floor of the cavity. The outlet of the pump is connected to a thermal pad that is stored inside the cavity when the therapy device is in the shipping configuration. The outlet of the pad drains into the cavity, where the fluid is recirculated through the pump. A compartment is defined between the insert and the inside of the box. The compartment receives the electrical cables, power supply, and control unit when the therapy device is in the shipping configuration. In the shipping configuration, the compartment is sealed with a closure. The closure is removed to expose an opening when the therapy device is in the deployed configuration, thereby allowing portions of the electrical components to be removed from the compartment.

In one embodiment, the insert is a solid material with insulation properties, such as a closed cell foam like Styrofoam. The insulated insert has a cavity divided into two regions. The bottom region is smaller than the upper region. The outside of the insulated insert adjacent the bottom region is dimensioned to fit inside the upper region of another insulated insert, thereby allowing multiple insulated inserts to be nested for shipping before being assembled to make a therapy device. The insulated insert has channels and notches for routing of the electrical cable between the cavity and the compartment and for routing the fluid lines from the cavity to outside the box. The insulated insert cooperates with an insulated cap attached to the inside surface of the lid of the container.

In another embodiment, the insert is formed from a planar sheet into a basket shape that nests inside the box. The shell insert has a cavity defined by sidewalls. The lip of the cavity has spacers, or connectors, with a flap that is attached to the box near the lip of the box. The electrical cable is routed through the space between connectors at an upper inside corner of the box as the cable is routed from the cavity to the space between the shell insert and the box. The cavity has a floor or bottom. The outside surface of the floor has a base extending from the surface to the inside bottom of the box. The base is a spacer that supports the shell insert at the floor. In one embodiment, a solid insulation, for example, a closed cell foam, is positioned between the inside surface of the box and the outside surface of the insert.

The shell insert is formed from a planar sheet that is waterproof. In various embodiments the sheet is a waterproof material or at least one surface of the sheet is coated with a waterproof material or a waterproof membrane is proximate at least one surface of the sheet. The sheet has a number of fold lines, such as scores or creases in the sheet, that aid in forming the sheet into a number of planar panels that are joined at the fold lines.

In another embodiment, the shell insert is a plastic sheet that fits inside a container and has insulating material between the insert and the container. In such an embodiment, the shell has a lip that engages the lip around the opening of the box. The insert is molded, such as by being vacuum formed. The insert has an integral pouring spout for emptying the cavity. The insert also has molded features for capturing the submersible pump, for securing the power cord from the pump as it is routed up the inside wall and passes into a compartment between the insert and the container, and a notch for allowing the fluid tubing to exit the container. In one embodiment, the insert has integral passages to allow an external strap to be partially stored inside the container.

In yet another embodiment, the shell insert is a plastic sheet that fits inside a container and has insulating material between the insert and the container. In such an embodiment, the shell has a lip that is sealed to an inside surface of the box. In one embodiment, the shell is sealed with a ribbon that is adhesively attached to both the lip of the shell and the inside surface of the box.

BRIEF DESCRIPTION OF THE SEVERAL VIEWS OF THE DRAWINGS

The above-mentioned features of the invention will become more clearly understood from the following detailed description of the invention read together with the drawings in which:

FIG. 12 is a cross-sectional view of the embodiment of the disposable therapy device shown in FIG. 10 showing the left inside of the insert cavity; and FIG. 13 is a top plan view of the embodiment of the insert shown in FIG. 10;

DETAILED DESCRIPTION OF THE INVENTION

Apparatus for a disposable portable thermal therapy device 100 is disclosed. The device is a compact, self-contained therapeutic device 100 suitable for patients to use in self-directed care. As used herein, the patient is an animal, which includes humans. As used herein, the A and B suffixes or the hash or apostrophe appended to a reference number indicate a particular embodiment of a component. When the reference number is used without the suffix, the generic component is being referenced, for example the device 100 refers generically to the therapy device, whereas 100-A, 100-B refer to specific embodiments of the device 100.

Figure 1:
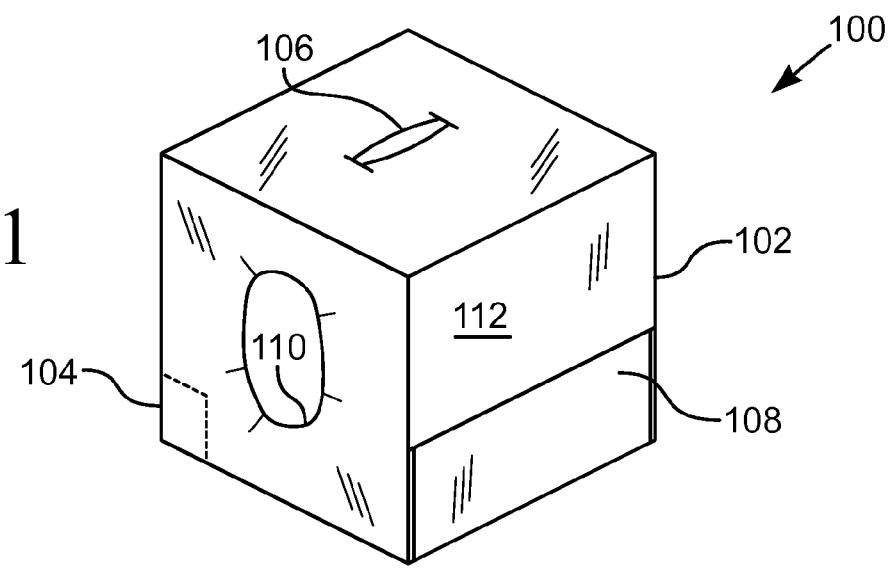
FIG. 1 is a perspective view of one embodiment of a disposable therapy device configured for shipping.

FIG. 1 illustrates a perspective view of one embodiment of a disposable therapy device 100 configured for shipping. The device 100 includes a container 102 that presents a polygon shape with six external sides. The illustrated configuration is with the therapy device 100 in a shipping configuration or state. The container 102 is enclosed in a wrap 108, such as a shrink wrap. The wrap 108 encloses the sides of the container 102 except for where the ends of the wrap 108 form an opening 110 on opposite sides of the container 102. For example, a polymer plastic film with a tubular shape sufficiently large enough for the container 102 to fit within is heat shrunk to enclose the container 102 with the ends 110 of the plastic film shrinking to substantially enclose the container 102. In another example, the plastic film is a sheet that is wrapped around the container 102 before heat is applied. In such an application the container 102 may be completely covered with no end openings 110.

In the illustrated embodiment, the container 102 has a handle 106 on the top surface. The illustrated handle 106 is a strap in which the ends fit into slots in the container 102. In one embodiment, the handle 106 is enclosed in the wrap 108 to aid in shipping and handling of the container 102 by avoiding protrusions from the surface of the container 102. In another embodiment, the handle 106 is outside the container 102 to allow the container 102 to be maneuvered by use of the handle 106.

Visible in a lower corner of the container 102 is an opening 104 with a perforated cover. In one such embodiment, the wall of the container 102 has a perforation that, when broken, creates an opening or portal 104 to the interior of the container 102. In other embodiments a removable plug covers the opening 104 until the opening 104 is desired to be used.

The container 102 has planar panels formed from a larger planar sheet that is bent and joined together. In various embodiments, the container 102 is a box fabricated of cardboard or other stiff planar material, such as a plastic or fiberboard. A corrugated material provides strength with light weight, and a solid material, such as pressed fiberboard, provides strength with minimal thickness. The planar material of the container 102 is folded or otherwise shaped to produce the desired configuration of the container 102. The container 102 has a closure 112, shown with the closure 112 sealing the container 102. The construction of the container 102 is such that it is suitable for shipping, handling, and storing the disposable therapy device 100. That is, the container 102 is sufficiently durable to survive the rigors of shipping, handling, and storage without damage to the components inside the container 102.

Figure 2:
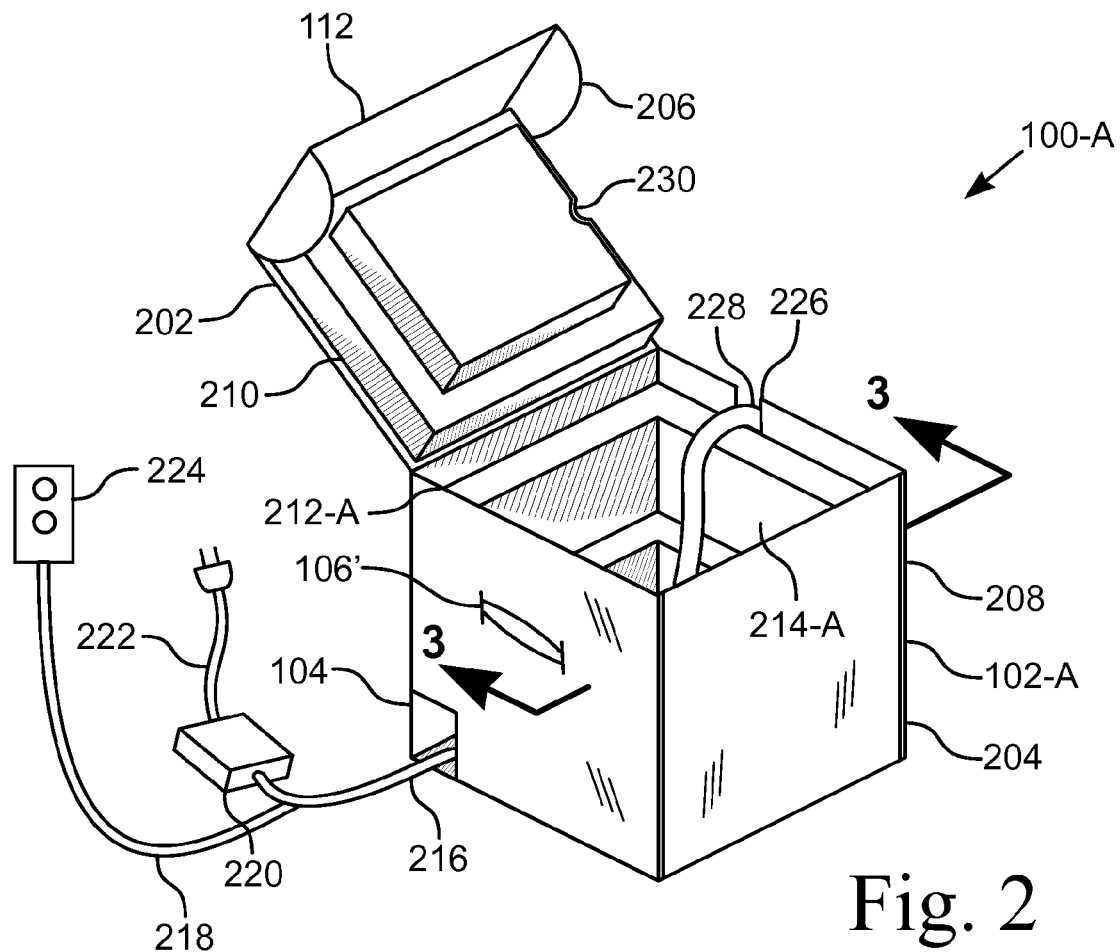
FIG. 2 is a perspective view of a disposable therapy device with various components removed from the container.

FIG. 2 illustrates a perspective view of one embodiment of a disposable therapy device 100-A with various components removed from the container 102-A. The illustrated embodiment of the disposable therapy device 100-A is shown in the operable configuration, that is, in a configuration ready for use to provide therapy. In the illustrated embodiment, the device 100-A includes a pair of handles 106' disposed on opposite sides of the container 102-A. The illustrated handle 106' is a strap in which the ends fit into slots in the container 102-A. In other embodiments, the handles are openings in opposite sides of the container 102-A, with the openings configured to receive the fingers of a person lifting the device 100-A. In yet another embodiment, a strap 1012 extending from one side to an opposite side is attached to the container 102-A and is suitable for lifting and moving the container 102-A.

The container 102-A includes a lid 202, shown in the open position, and a box 204. The box 204 has four sides, a bottom, and an open top. The top of the box 204 is covered by the lid 202, which includes the closure 112. On the lateral sides of the closure 112 are flaps 206 that fit into slots 208 on either side of the front of the box 204. When the flaps 206 engage the slots 208, the lid 202 is secured to the box 204. In this way, the handle 106 on top of the container 102-A is operable to lift the container 102-A without the lid 202 inadvertently opening. In another embodiment, the closure 112 is secured to the box 204 by a fastener or clasp. For example, a hook and loop fastener system releasably secures the closure 112 to the outside surface of the box 204, and the hook and loop fastener system has sufficient shear strength to prevent the lid 202 from disengaging the box 204 when a lifting force is applied to the lid 202.

Inside the box 204 is an insulated insert 212-A that has a cavity 214-A. In one embodiment, the cavity 214-A has a size sufficient to contain 8 to 10 liters of liquid. Attached to the inside surface of the lid 202 is an insulated cap 210 that engages and covers the opening in the insulated insert 212-A. When the lid 202 swings down to cover the box 204, the insulated cap 210 is configured to swing into position on top of the insulated insert 212-A. In one embodiment, the insulated insert 212 and cap 210 are a closed cell foam, such as Styrofoam, or other material that is suitable for providing temperature isolation between a water-ice mixture in the cavity 214-A and the ambient environment outside the container 102-A.

Visible in a lower right rear corner of the container 102-A is the opening 104 in which the perforated cover has been removed. Extending from the opening 104 is a cable 216 connected to a power supply 220, which is connected to a power cable 222 that is configured to connect to a power source, such as a 110 Vac wall socket. The power supply 220 converts the power from the power source to a voltage and/or current level that is suitable for use by the portable therapy device 100-A. In one embodiment, the cable 216 connects directly to a power source and the power supply 220 and power cable 222 are not used. In such an embodiment, the pump 312 and the control unit 224 do not require that the voltage of the power source be converted to another voltage level for use. For example, the pump 312 requires a 115 Vac supply and is electrically connected to the power cable 222, which plugs into a standard receptacle supplying 115 Vac.

The illustrated embodiment shows the cable 216 splitting before connecting to the power supply 220. The split-off control cable 218 has an end connected to a control unit 224. The control cable 218 has a length sufficient for an operator of the therapy device 100 to manipulate the controls on the control unit 224. For example, a patient wearing a pad 302 with the container 102 on the floor is able to operate the control unit 224.

In the illustrated embodiment, the cables 216, 218, the power supply 220 and the power cable 222, and the control unit 224, are removed from the container 102-A through the opening 104. In another embodiment, the power supply 220 remains in the container 102-A and the power cable 222 extends through the opening 104 along with the control cable 218.

The lip at the top of the box 204 has a slot or opening 226. A sheath 228 extends from the cavity 214 inside the insulated insert 212 through the slot 226. A corresponding notch 230 is formed in the insulated cap 210. The notch 230 provides clearance for the sheath 228 when the lid 202 is closed and the cap 210 engages the insulated insert 212.

Figure 3:
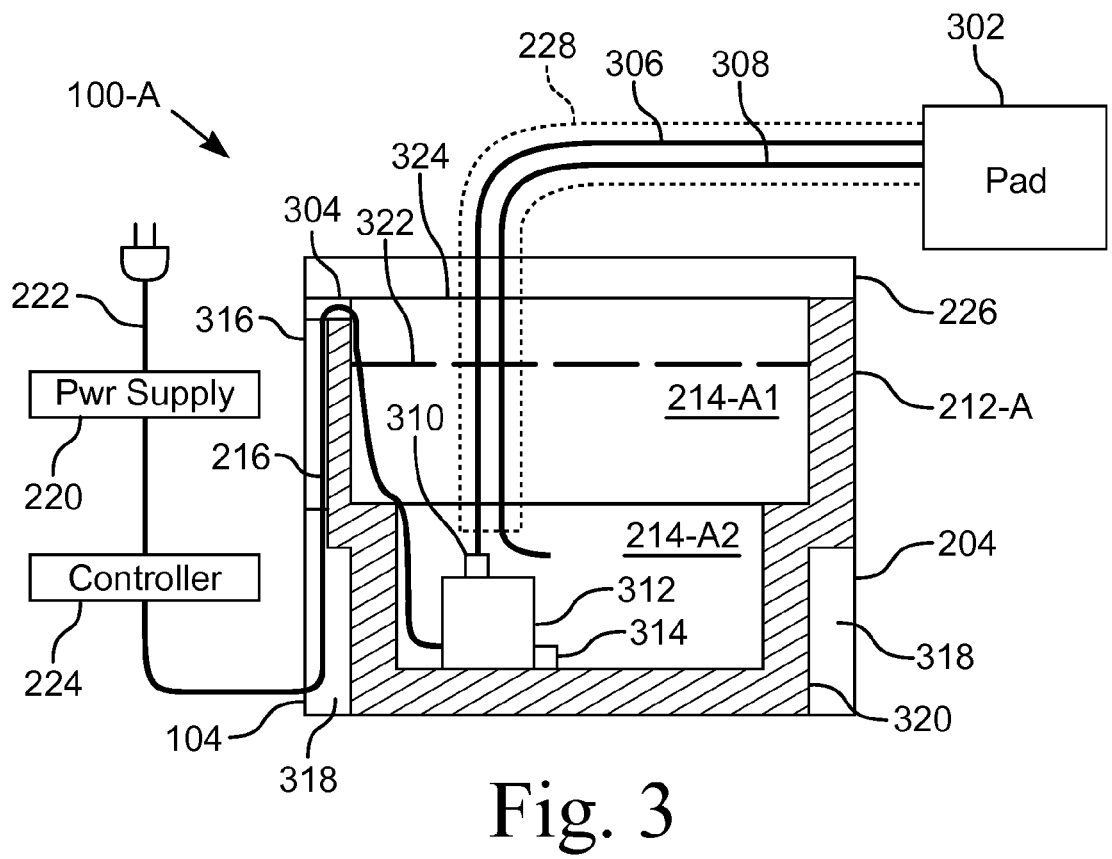
FIG. 3 is a cross-sectional view of one embodiment of a disposable therapy device showing one embodiment of an insulated insert.
Figure 4:
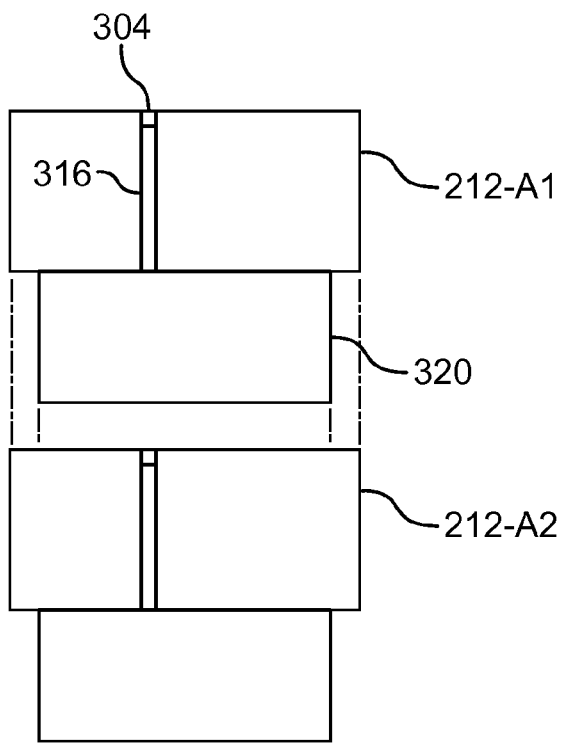
FIG. 4 is a pair of insulated inserts showing their nesting capability.

FIG. 3 illustrates a cross-sectional view of one embodiment of a disposable therapy device 100-A showing one embodiment of an insulated insert 212-A. FIG. 4 illustrates a pair of insulated inserts 212-A1, 212-A2 showing their nesting capability. FIGS. 2 and 3 illustrate the therapy device 100-A in the deployed configuration.

Each insulated insert 212-A has a first cavity 214-A1 and a second cavity 214-A2. The first cavity 214-A1 is dimensioned such that the outside surface of the insert 212-A has a sliding engagement with the inside surface of the box 204. In this way, the insert 212-A is readily positioned inside the box 204, yet rests inside the box with minimal movement relative to the sidewalls of the box 204.

The second cavity 214-A2 is joined to the first cavity 214-A1 to define one larger cavity 214-A. The second cavity 214-A2 is slightly smaller than the first cavity 214-A1. The second cavity 214-A2 is dimensioned such that the outside surface 320 of a first insulated insert 212-A1 fits into the first cavity 214-A1 of a second insulated insert 212-A2. The height of the outside surface 320 is approximately equal to the depth of the inside surface of the first cavity 214-A1, which ensures that the nested insulated inserts 212-A1, 212-A2 have a minimal storage height when nested, thereby aiding in minimizing storage and shipping space of the insulated inserts 212-A1, 214-A2.

The outside surface of one side of the insulated insert 212-A adjacent the first cavity 214-A1 has a groove 316 that connects with a notch, or slot, 304 on the lip 324 of the first cavity 214-A1. The cable 216 fits into the groove 316 and the notch 304 when the insulated insert 212-A is inside the box 204. That is, the groove 316 and the notch 304 define a passageway for the cable 216 between the inside surface of the box 204 and the insulated insert 212. In another embodiment, the groove 316 and notch 304 are located adjacent a corner of the insulated insert 212-A.

Inside the second cavity 214-A1 is a pump 312. In one embodiment the pump 312 is attached to the inside bottom surface of the insulated insert 212-A, such as by attaching to a bracket fixed to the surface or by attaching the pump 312 directly to the surface, for example, with an adhesive or fasteners. In the illustrated embodiment, the pump 312 is a submersible unit configured to be operated while submerged in a liquid. The pump 312 is an electrically driven device that receives electric power from the cable 216 and operates, when electrically energized, by receiving water from an intake port 314 and discharging that water through an exhaust, discharge, or outlet, port 310. In the illustrated embodiment the intake port 314 is separated from the discharge port 310, although in other embodiments the separation varies to accommodate fluid mixing requirements.

The exhaust port 310 of the pump 312 is connected to a supply line 306 that is connected to the intake of a thermal pad 302. The outlet of the thermal pad 302 is connected to a return line 308 that discharges inside the cavity 214-A. The supply and return lines 306, 308 are inside the sheath 228, which carries the lines 306, 308 as they are routed from the cavity 214-A to the thermal pad 302. The return line 308 is not connected to anything in the illustrated embodiment, but discharges into the cavity 214-A directly. In another embodiment, the end of the return line 308 is fixed inside the cavity 214-A to anchor the line 308 and to ensure that the warmed water discharged from the return line 308 is directed in a selected manner. In one embodiment, the supply and return lines 306, 308 are joined in a single, integral pair of conduits. As such, the sheath 228 is not necessary to keep the supply and return lines 306, 308 together as they run between the cavity 214-A and the pad 302.

The thermal pad 302 is a device that is configured to be positioned adjacent a portion of the patient's body. The thermal pad 302 includes flat pads and shaped pads, both of which include fluid channels that allow the fluid from the supply line 306 to flow through the pad and exit through the return line 308. The therapy pad 302 provides for heat transfer between the patient's body and the fluid flowing from the cavity 214-A. In one embodiment, the lines 306, 308 are releasably attachable to the pad, such as with connectors.

The cable 216 is connected to the pump 312 at one end. The cable 216 is routed along the inside surfaces of the insulated insert 212-A, through the notch 304, along the channel 316 and into the compartment 318. The compartment 318 is the volume between the inside surface of the box 204 and the outside surface 320 of the insulated insert 212. The cable 216 exits the opening 104 in the container 102. FIG. 3 symbolically illustrates the cable 316 connected to the controller, or control unit, 224, which is connected to the power supply 220, which is connected to the power cable 222. The power from the power supply 220 is controlled by the control unit 224 to operate the pump 312. In various embodiments the control unit 224 includes controls to energize and de-energize the therapy device 100 and/or a timer for controlling the operating time and/or the duty cycle of the therapy device 100. In another embodiment, the human operated controls, for example the on/off switch, is on a device remote to the control unit 224 and the device is in communication with the control unit 224, such as through a cable or wireless connection.

As used herein, the control unit 224 should be broadly construed to mean any device that accepts inputs and provides outputs based on the inputs, for example an analog control device, an application specific integrated circuit (ASIC), a microcontroller, or a computer or component thereof that executes software. In various embodiments, the control unit 224 is one of a specialized device or a computer for implementing the functions of the invention. The control unit 224 includes input/output (I/O) units for communicating with external devices and a processing unit that varies the output based on one or more input values. The input component of the control unit 224 receives input from external devices, such as temperature sensors and control button positions, such as those indicating on, off, timer, and duty cycle. The output component sends an output signal to external devices, such as the pump 312. In yet another embodiment, the control unit 224 is a switch that controls power to the pump 312.

The disposable therapy device 100 is self-contained and suitable for shipping in the configuration illustrated in FIG. 1. The various components illustrated in FIG. 3 that are shown outside the container 102-A are inside for shipping. The cable 316, the controller 224, the power supply 220, and the power cable 222 are stored in the compartment 320. The pump 312, the sheath 228 with the two lines 306, 308, and the thermal pad 302 are stored in the cavity 214. With the opening 104 covered and the lid 202 covering the box 204, the therapy device 100 is self-contained. To aid in preventing damage during shipping, the cavity 214 also contains packing material around the pump 312, the sheath 228, and the pad 302.

Preparing the disposable therapy device 100 for use includes removing the wrap 108 from the container 102. The perforated cover is removed from the opening 104 and the controller 224 and the power cable 222 are removed from the compartment 318 through the opening 104. In one embodiment, the power supply 220 remains inside the compartment 318, as does the cable 216. In another embodiment, the power supply 220 and a portion of the cable 216 are removed from the compartment 318, along with the controller 224 and its cable 218. In another embodiment, the pump 312 is directly connected to the power cable 222 and the pump 312 operates whenever power is supplied to the power cable 222. In one such embodiment, an in-line switch is incorporated in the power cable 222. In yet other embodiments, the cable 216 is connected to the power supply via a connector and/or the controller is connected to the control cable 218 via a connector. The power supply 220 and power cable 222 and/or the controller 224 are then stored in the cavity 214 during shipping and removed and connected to their respective cables 216, 218 when preparing for use.

Preparing the device 100 for use also includes opening the lid 202 and removing the pad 302 and the end of the sheath 228 from the cavity 214. If the pump 312 is not attached to the inside of the insulated insert 212, the pump 312 is secured to a bracket or clip fixed to the inside of the insert 212.

In operation, a user fills the cavity 214 to the fill line 322 with a mixture of water and ice. The ice may be chips, cubes, chunks, or a block. Additives or other substances may also be mixed with the water. The fill line 322 is indicia that indicates an optimum level of fluid in the cavity 214. The user, after ensuring that the controller 224 is in the off position if it has a mechanical type switch, connects the power plug 222 into a power source, such as the 115 Vac mains or a battery. The pad 302 is applied to the body portion to be treated. The controller 224 is then operated to cause the fluid in the cavity 214 to flow through the pad 302.

Figure 5:
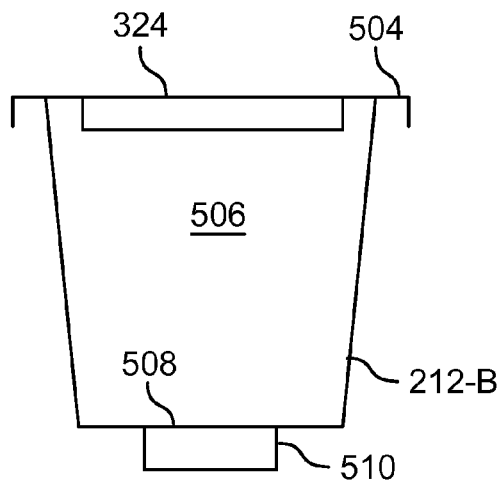
FIG. 5 is a side view of another embodiment of an insert.
Figure 6:
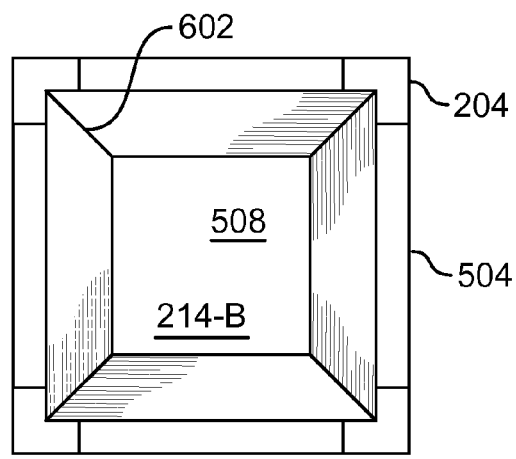
FIG. 6 is a top view of the insert in the cooler box.

FIG. 5 illustrates a side view of another embodiment of an insert 212-B. FIG. 6 illustrates a top view of the shell insert 212-B in the box 204. The shell insert 212-B has the general shape of an inverted, truncated 4-sided pyramid, that is, it has a basket shape. The shell insert 212-B has four sidewalls 506 and a floor, or bottom, 508. The inside of the shell insert 212-B defined by the four sidewalls 506 and the floor, or bottom, 508 is a cavity 214-B. The sidewalls 506 are separated by a crease 602. Extending from the lip 324 of the shell insert 212-B at each sidewall 506 is a connector, or upper spacer, 504. The connector 504 has a flap 702 that attaches to the inside surface of the box 204 to secure the shell insert 212-B in the box 204.

Adjacent the floor 508 and on the outside surface of the shell insert 212-B is a base 510. The base 510 is a spacer that separates the floor 508 from the inside bottom surface of the box 204. In various embodiments, the bottom base, or spacer, 510 is hollow and has a cylindrical-shape, a polygonal-shape, or other configuration that supports the remainder of the shell insert 212-B above the inside bottom of the box 204. In one embodiment, the spacer 510 is an insulation material, such as a closed cell foam.

The shell insert 212-B, in combination with the box 204, forms a cavity 214-B that is insulated. The air gap between the inside surfaces of the box 204 and the outside surfaces of the shell insert 212-B is an insulator. Conduction is minimized by limiting the contact between the box 204 and the shell insert 212-B to only the connectors 504 and the base 510. In another embodiment, insulating material is placed in the air gap between the box 204 and the shell insert 212-B except for a volume that defines the compartment 318 for storing the electrical components 216, 222, 218, 224. For example, expanding foam is injected in the upper portion of the volume, leaving the compartment 318 below unobstructed. In another example, pieces of insulation material, such as closed cell foam, are positioned in the space between the box 204 and the insert 212-B.

With the insert 212-B in the box 204, one of the gaps between adjacent upper spacers 504 is a passageway for the cable from the pump 312 to the compartment 318 between the box 204 and one of the sidewalls 506 of the insert 212-B. With the pump 312 secured to the bottom 508 of the insert 212-B, the cable is routed in the corner of the insert 212-B and through the gap, or passageway, between adjacent spacers 504 into the space between the box 204 and the insert 212-B.

Figure 7:
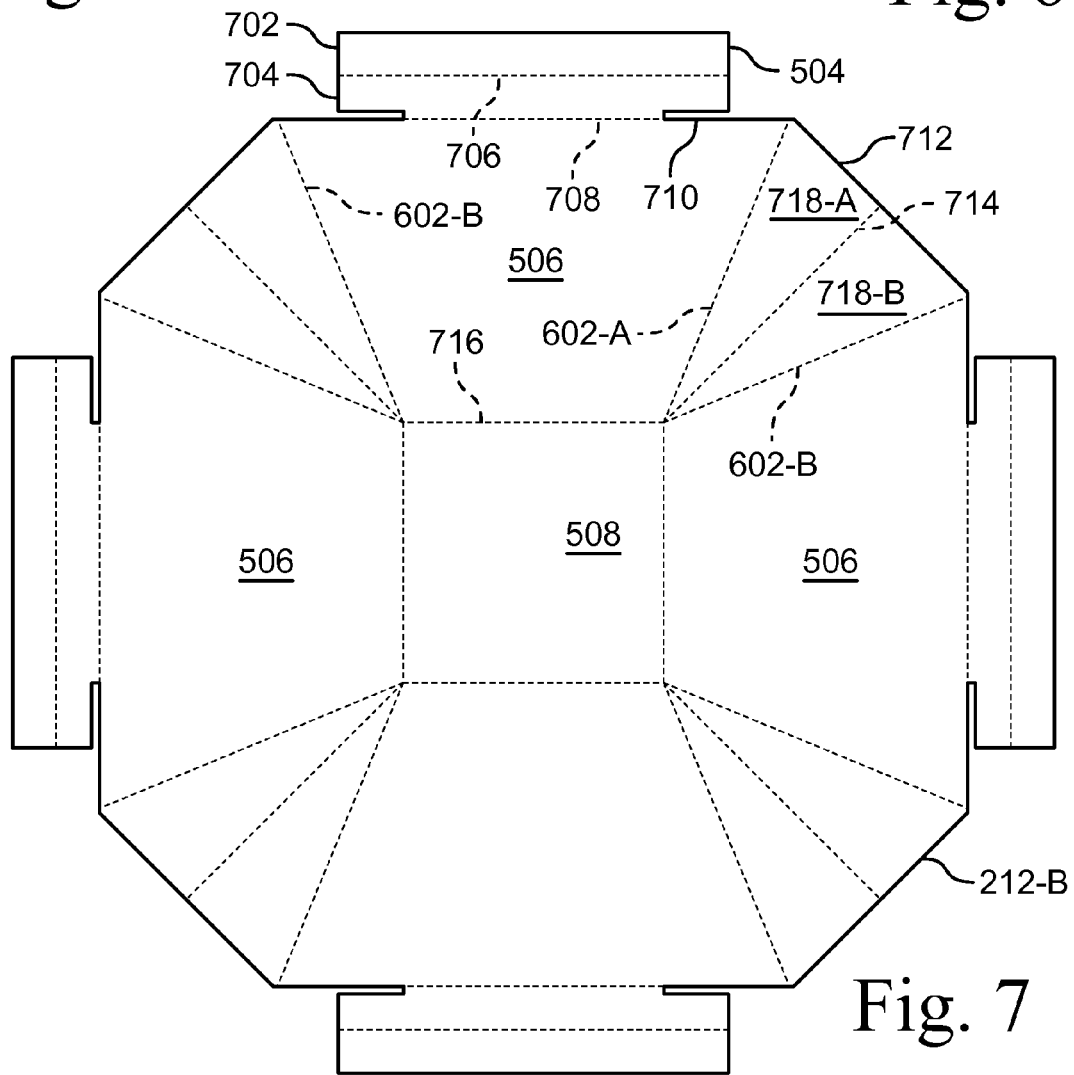
FIG. 7 is a plan view of one embodiment of an insert before it is folded into a basket-shape.
Figure 8:
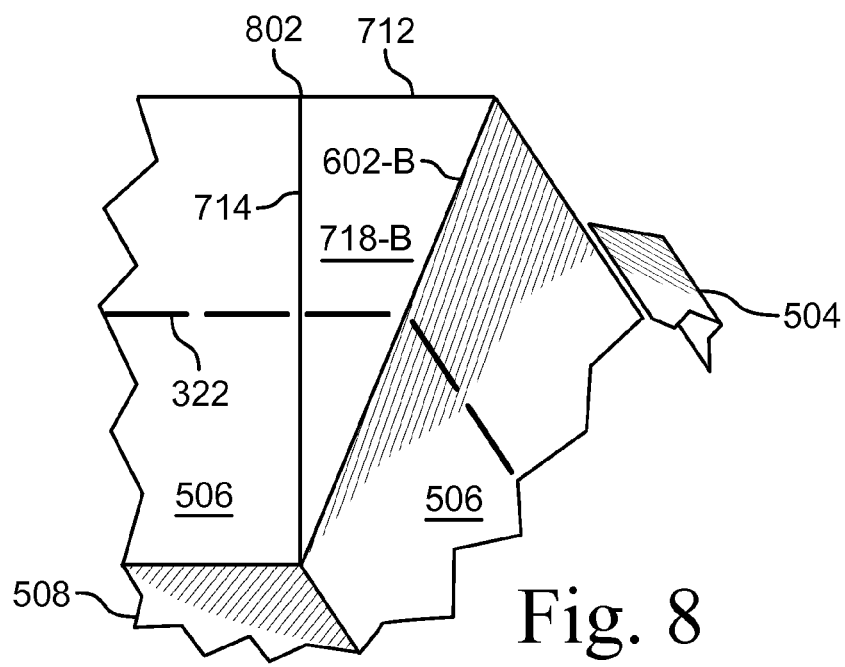
FIG. 8 is a partial inside view of the insert.

FIG. 7 illustrates a plan view of one embodiment of a shell insert 212-B before it is folded into a basket-shape. FIG. 8 illustrates a partial inside view of the insert 212-B. The shell insert 212-B in its non-deployed state as shown in FIG. 7, is a planar sheet that is impervious to water and fluids on at least one side.

In various embodiments, the shell insert 212-B is fabricated of cardboard or other stiff planar material, such as a plastic or fiberboard. The surface of the shell insert 212-B that defines the cavity 214-B, in one embodiment, is coated with a layer or has a membrane on the surface that is a polymer or other material that is water proof or water-resistant. In its deployed state, the shell insert 212-B is watertight such that the insert 212-B is able to contain a liquid, such as water, without leakage. The shell insert 212-B has fold lines, for example the fold lines 716 that define the floor 508. The fold lines, in one embodiment, are scores or creases in the planar material that create weakened areas that allow the planar material of the shell insert 212-B to fold into two intersecting panels at the fold line. The planar material of the shell insert 212-B is folded or otherwise shaped to produce the desired configuration of the shell insert 212-B.

The connectors 504 of the shell insert 212-B have a flap 702 that is outboard of an extension 704. The flap 702 is separated from the extension 704 by a fold line 706 that allows the flap 702 to be positioned at an angle to the extension 704. The flap 702 has a surface area that is sufficient to attach to the inside surface of the box 204, such as with an adhesive or a fastener. The extension 704 is separated from the sidewall 506 by a fold line 708 that allows the extension 704 to be positioned at an angle relative to the sidewall 506. The extension 704 is not connected to the sidewall 506 along the full length of the extension 704, but is also separated from the sidewall 506 by a pair of slots 710. The slots 710 minimize the conduction from the cavity 214-B to the box 204 and the length of the fold line 708 is sufficient to provide enough mechanical strength to support the shell insert 502 in the box 204.

In another embodiment, the connectors, or spacers, 504 have three panels having a substantially U-shape. One panel 702 is attached to an inside surface of the box 204, the middle panel 704 bridges the gap between the inside surface of the box 204 and the lip 324, and the third panel is attached to a sidewall panel 506 adjacent the lip 314. In yet another embodiment, the connector 504 is a spacer that separates the box 204 from the lip 324 while physically connecting the two 204, 324. In these ways, the connectors, or spacers, 504 function similarly to the connector 504 illustrated in FIG. 7, which shows the connectors 504 being unitary with the insert 502.

The sidewalls 506 are defined by four fold lines 708, 602-A, 602-B, 716. Adjacent to and between pairs of sidewalls 506 are a pair of corner panels 718-A, 718-B. The two corner panels 718-A, 718-B are separated by a fold line 714. The opposite edge of each corner panel 718-A, 718-B is separated from its adjacent sidewall panel 506 by a fold line 602-A, 602-B.

To form the basket shape of the shell insert 212-B, the two corner panels 718-A, 718-B are brought together such that the fold line 714 protrudes into the cavity 214-B being formed. At the same time, each of the fold lines 716 between the sidewall panels 506 and the bottom panel 508 define the apex of the two panels 506, 508 as the material of the insert 212-B is bent. One corner panel 718-A is brought adjacent a sidewall panel 506 and laid flat against the inside surface of a sidewall 506 as illustrated in FIG. 8. The corner 802 formed by the juncture of the center fold line 714 and the edge 712 between the connectors 504 is in-line with the lip 324 of the cavity 214-B, which is where the fold line 708 between the sidewall 506 and the extension 704 is located. Accordingly, the cavity 214-B is waterproof up to the lip 324.

In another embodiment, there is only one corner panel 718-B that is attached to a sidewall panel 506. There is a wedge-shaped gap between the corner panel 718-B and the other adjacent sidewall panel 506. The corner panel 718-B is a flap that is then adhesively attached to the other adjacent sidewall panel 506. For example, the inside surface of the other adjacent sidewall panel 506 is adhered to the corresponding surface of the corner panel 718-B with the adhesively joined joint forming a water-tight seal between the adjacent sidewall panels 506. In another embodiment, the cavity 214-B is lined with a layer that is water tight.

Figure 9:
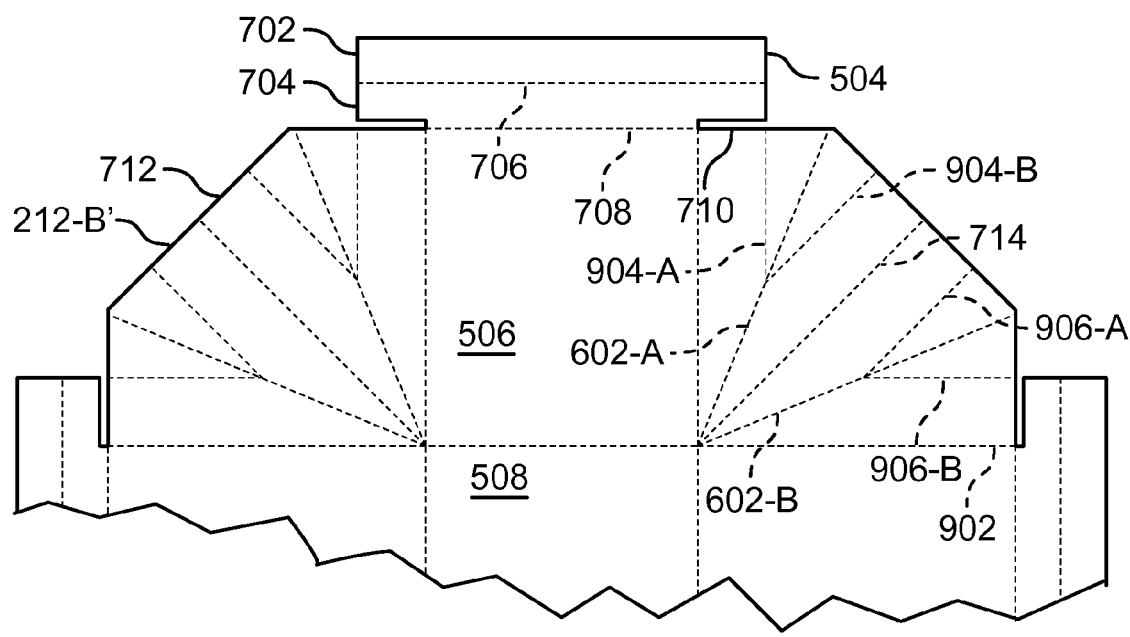
FIG. 9 is a partial plan view of another embodiment of an insert before it is folded into a basket-shape.

FIG. 9 illustrates a partial plan view of another embodiment of an insert 502' before it is folded into a basket-shape. The illustrated embodiment is similar to that illustrated in FIG. 7, with the addition of additional fold lines 902, 904-A, 904-B, 906-A, 906-B. The additional fold lines 904-A, 904-B, 906-A, 906-B allow the corners of the shell insert 502' between the sidewalls 506 to more closely conform to the corners of the box 204, thereby increasing the volume contained by the cavity 214-B.

Figure 10:
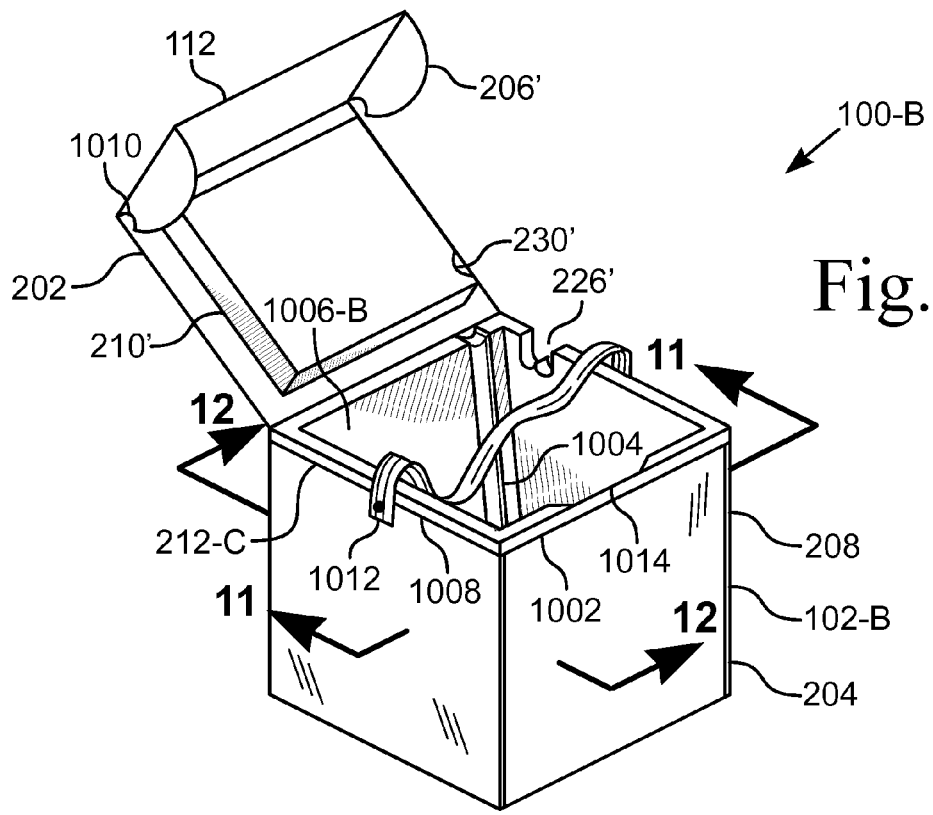
FIG. 10 is a perspective view of another embodiment of a disposable therapy device showing another embodiment of the container and yet another embodiment of an insert.

FIG. 10 illustrates a perspective view of another embodiment of a disposable therapy device 100-B showing the container 102-B and yet another embodiment of an insert 212-C. In the illustrated embodiment, the device 100-B includes a strap 1012 that extends between the left and the right sides. The strap 1012 is stowable inside the cavity 214-C when the lid 202 is closed.

The container 102-B includes a lid 202, shown in the open position, and a box 204. The top of the box 204 is covered by the lid 202, which includes the closure 112. On the lateral sides of the closure 112 are flaps 206' that fit into slots 208 on either side of the front of the box 204. When the flaps 206' engage the slots 208, the lid 202 is secured to the box 204. The flaps 206' each include a notch 1010 positioned to allow the flaps 206' to clear the lip 1008 of the insert 214-C. The lip 1008 extends downward from the top of the box 204. The notches 1010 are dimensioned such that the portion of the lip 1008 that covers the slots 208 fits into the notches 1010 when the closure 112 is closed.

An insulator 210' is attached to the surface of the lid 202 that is proximate the insert 212-C when the lid 202 is closed. The insulator 210' is sized to mate with the top portion of the insert 212-C. The upper edge of the box 204 and insert 212-C has a slot or opening 226'. The insulator 210' includes a corresponding notch 230'. The notch 230' provides clearance for the sheath 228 when the lid 202 is closed and the insulator 210' engages the insert 212-C.

Inside the box 204 is an insert 212-C. The insert 212-C includes four walls 1006, a floor 1106, and a lip 1008. The walls 1006 and floor 1106 define a cavity 214-C for holding a liquid. In one embodiment, the cavity 214-C has a size sufficient to contain 8 to 10 liters of liquid, such as an ice-water mixture. The lip 1008 extends from the cavity 214-C, over the top edges of the front and side walls 1006-F, 1006-L, 1006-R of the box 204, and a short distance downward on the outside of the box 204.

Figure 11:
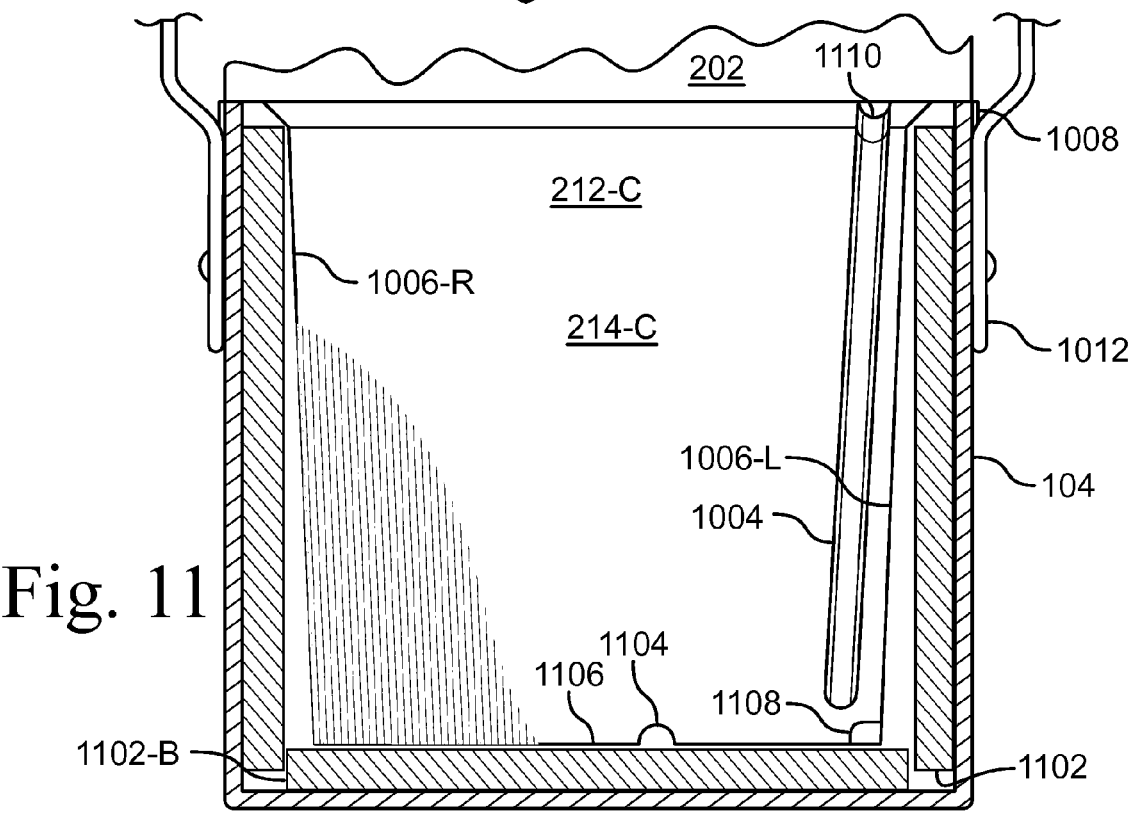
FIG. 11 is a cross-sectional view of the embodiment of the disposable therapy device shown in FIG. 10 showing the rear of the insert cavity.

FIG. 11 illustrates a cross-sectional view of the embodiment of the disposable therapy device 100-B of FIG. 10 showing the rear wall 1006-B of the insert cavity 214-C. FIG. 12 illustrates a cross-sectional view of the embodiment of the disposable therapy device 100-B of FIG. 10 showing the left inside wall 1006-L of the insert cavity 214-C. FIG. 13 illustrates a top plan view of the embodiment of the insert 212-C shown in FIGS. 10-12.

The box 204 has a rectangular configuration. In one embodiment, the walls of the box 204 are corrugated cardboard. Inside the box 204 and lining the walls are flat sections of insulation 1102. In one embodiment, the pieces of insulation 1102 are flat sections of closed cell foam, such as Styrofoam, that are one-half inch (12 mm) thick. In one embodiment, the insulation 1102 is adhesively fixed to the inside surfaces of the box 204.

The illustrated insert 212-C is a rigid plastic-type material that is molded, such as by a vacuum-forming process. The insert 212-C fits inside the box 204 with the insulation 1102 between the walls 1006 of the insert 212-C and the box 204. In the illustrated embodiment, the left and right walls 1006L, 1006-R of the insert 212-C are slanted to aid in the insertion of the insert 212-C into the box 204. The floor 1106 of the insert 212-C rests on the bottom insulation 1102-B. The lip 1008 of the insert 212-C rests on the upper edge of the box 204. In the illustrated embodiment, a beveled interface connects the walls 1006 of the insert 212-C to the lip 1008.

The back wall 1006-B of the insert 212-C has an angle sufficient to define a compartment 318 between the lower portion of the back wall 1006-B and the rear insulation 1102-R. The opening 104 in the box 204 provides a passage from the compartment 318 to outside the box 204. The compartment 318 is sized to store the cord from the pump 312. In another embodiment, the back wall 1006-B has a step or is non-planar such that a lower portion of the back wall 1006-B is separated from the rear insulation 1102-R by a distance larger than the separation of the upper portion of the back wall 1006-B to the rear insulation 1102-R.

Visible on the back, or rear, wall 1006-R of the insert 212-C is a gutter or trough 1004 sized to receive the cord, or cable, from the pump 312. The gutter 1004 is a passageway for the cable from the pump 312 to the compartment 318. One end of the gutter 1004 extends toward the floor 1106 of the insert 212-C. The opposite end of the gutter 1004 terminates at an opening 1110. The opening 1110 is adjacent the lip of the insert 212-C and allows passage of the cord from the cavity 214-C to the compartment 318 between the insert 212-C and the box 204. The cord is stored in the compartment 318 until the therapy device 100-B is deployed for use. The cover of the opening 104 is removed and the power plug end of the cord is removed from the compartment 318 through the opening 104. In one embodiment, the pump 312 is supplied with 115 vac power from the power cord 222, which plugs directly into a standard household power receptacle. In one embodiment, the cord 222 has an in-line switch to control the pump 312. In one embodiment of the gutter 1004, the edge of the gutter 1004 proximate the back wall 1006-B of the insert 212-C is configured to grip the cord when received by the gutter 1004. For example, the gutter 1004 includes a series of protrusions by the interface that present an opening that is narrower than the inside width of the gutter 1004. In another example, the cord is fixed in the gutter 1004 with an adhesive.

The front wall 1006-F of the insert 212-C includes a spout 1014. When the cavity 214-C contains liquid, the spout 1014 allows the liquid to be drained from the cavity 214-C by tilting the box 204 forward so that the top of the spout 1014 is below the fluid level. The front wall 1006-F has a planar portion that connects to the adjacent walls 1006-L, 1006-R and the floor 1106. Located centrally between the adjacent walls 1006-L, 1006-R is the spout 1014, which includes a portion of the front wall 1006-F that forms a trough that directs liquid from the cavity 214-C out of the insert 212-C. The front insulation 1102-F positioned between the front wall 1006-F of the insert 212-C and the front wall of the box 204 has a configuration to accommodate the spout 1014. For example, in the illustrated embodiment, the front insulation 1102-F is shorter proximate the spout 1014. In another embodiment, the front insulation 1102-F has a varying thickness that is dimensioned to accommodate the space between the front wall 1006-F of the insert 212-C and the box 204.

Adjacent the gutter 1004 on the left wall 1006-L of the insert 212-C is an opening 226' that is sized to receive the sheath 228 or the two lines 306, 308 that go to the pad 302. The opening 226' cooperates with the notch 230' in the insulator 210' attached to the lid 202. The opening 226' is sized to accommodate the sheath 228 or the two lines 306, 308 with the lid 202 closed. In one such embodiment, the upper edge of the box 204 proximate the opening 226' has a corresponding opening such that the lip 1008 of the insert 214-C rests evenly on the upper edge of the box 204.

Proximate the gutter 1004 and the opening 226' on the floor 1106 of the insert 212-C is a space 1302 for the pump 312. The space 1302 is defined by a bar 1104 and two protrusions 1108 extending upwards from the floor 1106. The bar 1104 and protrusions 1108 are positioned and sized to receive a base of the pump 312, which is secured in the space 1302. In one such embodiment, the pump 312 is fixed in the space 1302 with an adhesive.

In one embodiment, the pump 312 is secured to the floor 1106 and the power cord is routed in the gutter 1004, through the opening 1110, and into the compartment 318. The exhaust port 310 of the pump 312 is connected to a supply line 306 that is connected to the intake of a thermal pad 302. The outlet of the thermal pad 302 is connected to a return line 308 that discharges inside the cavity 214-C. The supply and return lines 306, 308 are inside the sheath 228, which carries the lines 306, 308 as they are routed from the cavity 214-C to the thermal pad 302 through the opening 226'.

The illustrated embodiment includes a strap 1012 that is attached to opposite sides of the box 204 with a fastener, such as a rivet. In another embodiment, the ends of the strap 1012 extend under the lip 1008 into the box 204. The end of the strap 1012 inside the box 204 is attached to the box 204 and to a medial portion of the strap 1012 that loops down from the lip 1008 and upwards. The lip 1008 on the left and right sides of the insert 212-C include depressions 1202 that are sized to receive the strap 1012 when the strap 1012 is stored inside the cavity 214-C with the lid 202 closed. In one such embodiment, the upper edge of the box 204 proximate the depressions 1202 have a corresponding depression such that the lip 1008 of the insert 214-C rests evenly on the upper edge of the box 204.

Figure 14:
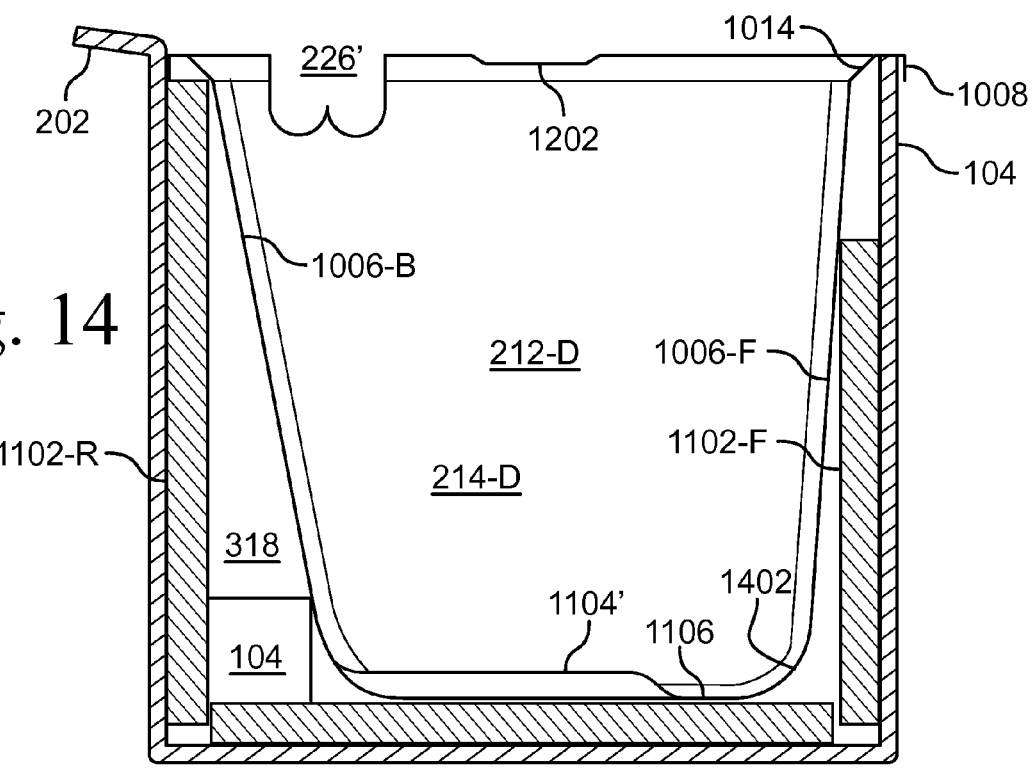
FIG. 14 is a cross-sectional view of yet another embodiment of the insert showing the left inside of the insert cavity.
Figure 15:
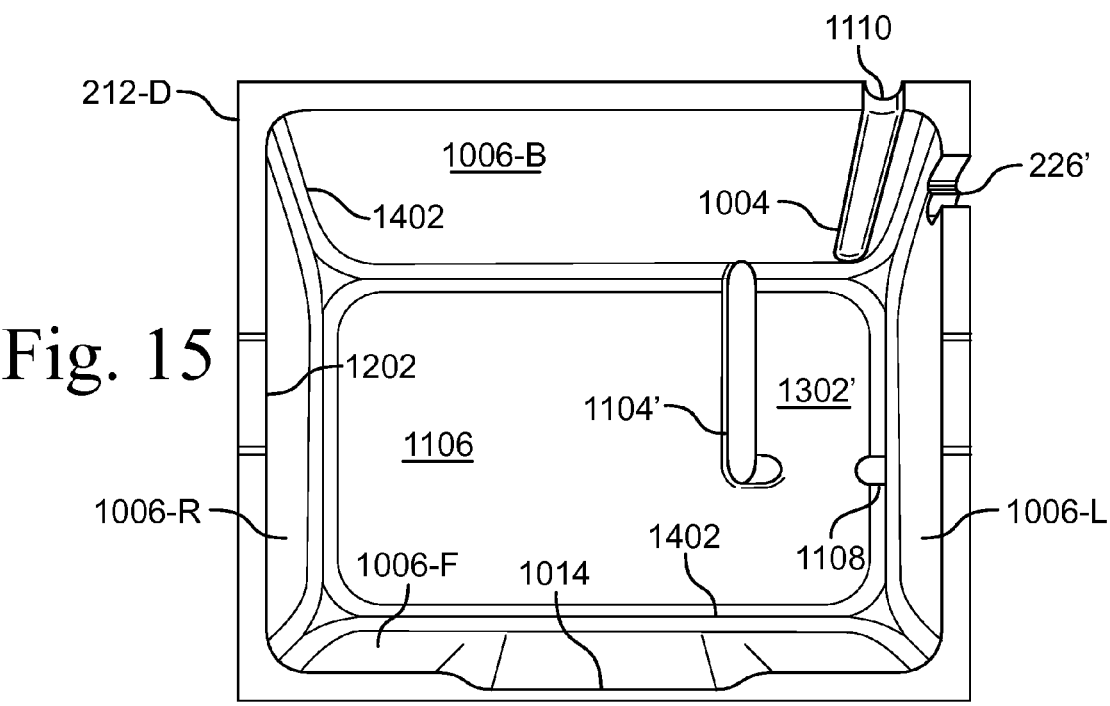
FIG. 15 is a top plan view of the embodiment of the insert shown in FIG. 14.

FIG. 14 is a cross-sectional view of another embodiment of the insert showing the left inside of the insert cavity 214-D. FIG. 15 is a top plan view of the embodiment of the insert shown in FIG. 14. The illustrated embodiment of the insert 212-D differs from the embodiment of the insert 212-C illustrated in FIG. 12 by the configuration of the connections of the walls 1006 and the floor 1106 and by the configuration of the space 1302'. In the illustrated embodiment, the insert 212-D has radiused corners 1402 where the four walls 1006 and the floor 1106 meet. In one embodiment, the corners 1402 have a radius of 1 inch (25 mm).

The illustrated insert 212-D is a rigid plastic-type material that is molded, such as by a vacuum-forming process. The walls 1006 and floor 1106 are substantially planar. The walls 1006 and the floor 1106 are joined together with rounded corners 1402 without a distinct edge. The continuous surface formed by the rounded corners 1402 assists in the manufacturability of the insert 212-D. It also aids in the mixing of the contents of the cavity 214-D, such as when the cavity 214-D contains an ice and water mixture.

FIG. 15 illustrates another embodiment of the space 1302' that receives the pump 312. The bar 1104' protrudes from the floor 1106. One end of the bar 1104' intersects with the back wall 1006-B with a radiused connection. The opposite end of the bar 1104' has an L-shape with a protrusion that lines up with the protrusion extending from the left wall 1006-L. The surfaces of the bar 1104' and the protrusion 1108 that define the space 1302' for the pump 312 are substantially perpendicular to the surface of the floor 1106. In this way the pump 312 better fits in the space 1302' and is secured laterally by the substantially perpendicular surfaces of the bar 1104' and the protrusion 1108. Those skilled in the art will recognize that the configuration of the bar 1104' and the protrusion 1106 will vary depending upon the configuration of the base of the pump 312. The surfaces of the bar 1104' and the protrusion 1108 opposite the space 1302' connect to the walls 1006-B, 1006-L and the floor 1106 with a radiused or contoured joint.

Figure 16:
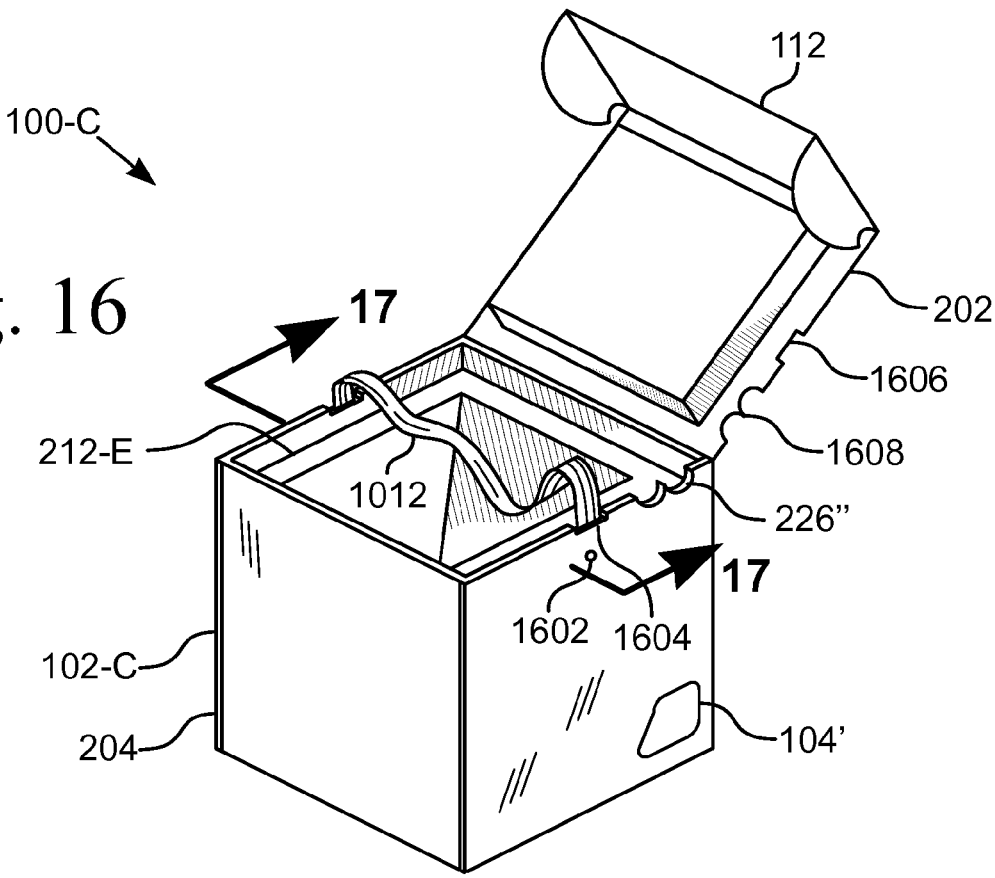
FIG. 16 is a perspective view of another embodiment of a disposable therapy device showing another embodiment of the container and yet another embodiment of an insert.

FIG. 16 illustrates a perspective view of another embodiment of a disposable therapy device 100-C showing the container 102-C and yet another embodiment of an insert 212-E. The container 102-B includes a lid 202, shown in the open position, and a box 204, similar to that illustrated in FIG. 10. Inside the box 204 is an insert 212-E that fits inside box 204 with the upper lip 1806 of the insert 212-E below the upper lip of the box 204. With the lid 202 closed and covering the opening on top of the box 204, the device 100-C is in the closed configuration. In such closed configuration and with the strap 1012 positioned adjacent the outer surface of the lid 202, the device 100-C presents a configuration that occupies a rectangular solid space with minimal protrusions that would prevent other devices 100-C from being positioned adjacent the device 100-C in a compact arrangement for shipping and storage.

In the illustrated embodiment, the device 100-C includes a strap 1012 that extends between the left and the right sides. Each end of the strap 1012 is positioned inside a corresponding sidewall of the box 204 and secured with a fastener 1602, such as a rivet. The upper lip of the box 204 has a strap notch 1604 and the lid 202 has a corresponding notch 1606 that, together, allow the strap 1012 to extend outside the box 204 with the lid 202 closed. The two notches 1604, 1606 provide clearance for the strap 1012 while allowing the lid 202 to fit snugly to the box 204. The strap 1012 is stowable outside the device 100-C when the lid 202 is closed. In one embodiment, when the strap 1012 is stowed outside the device 100-C it is folded over such that the strap 1012 lies flat against the lid 202. In another embodiment, the strap 1012 has a buckle that allows the length of the strap 1012 to be shorted such that the strap 1012 lies flat against the lid 202.

The box 204 has an opening 226" that coincides with a corresponding opening 1608 in the lid 202. The box 204 with the lid 202 closed forms a joint with a passageway 226", 1608 for the sheath 228 or the two lines 306, 308. The openings 226", 1608 are configured and sized to accommodate the sheath 228 or the two lines 306, 308 with the lid 202 closed. On the side of the box 204 is an opening 104' with a perforated cover. The opening 104' is configured and sized to provide a passageway into the compartment 318 between the box 204 and the insert 212-E.

Figure 17:
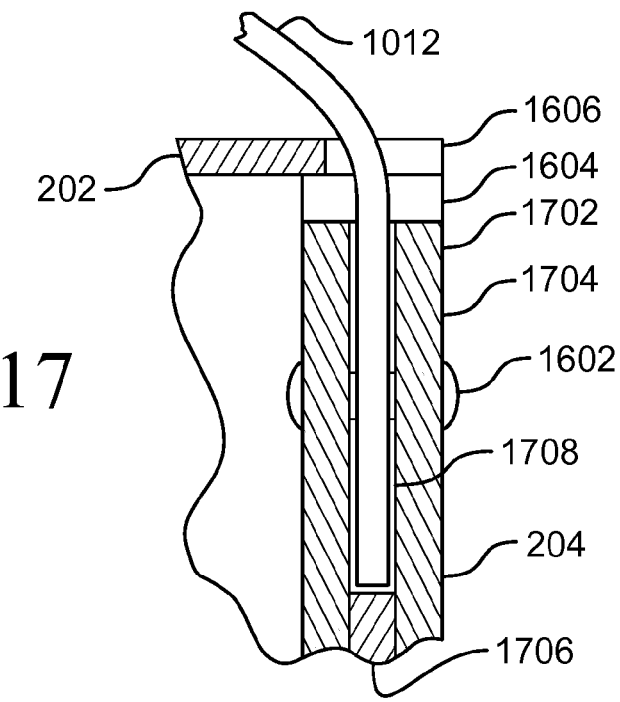
FIG. 17 is a cross-sectional view of one embodiment of a strap extending from a sidewall.

FIG. 17 illustrates a cross-sectional view of one embodiment of a strap 1012 extending from a sidewall 1702 of the box 204. The sidewall 1702 in the illustrated embodiment includes a sheet 1704 that is folded into parallel panels with the fold at the top of the box 204. Between the two panels of the sheet 1704 is a spacer 1706 that defines a cavity 1708 into which an end of the strap 1012 fits. The end of the strap 1012 is secured in the cavity 1708 with a fastener 1602 that penetrates the two panels of the sheet 1704 and the strap 1012. In the illustrated embodiment the fastener 1602 is a rivet with a low-profile head that does not protrude a substantial distance from the sheet 1704. The low-profile fastener 1602 enables multiple devices 100-C to be stacked side-by-side in a minimum amount of space with no wasted space between devices 100-C, which results in a high packing density for storage and shipping. The joint between the box 204 and the lid 202 in the closed configuration defines a passage 1604, 1606 for the strap 1012 to pass through. In this way with the device 100-C in the closed configuration the sidewalls 1702 of the box 204 and the lid 202 will not be deformed when the handle 1012 is used to carry the weight of the device 100-C.

Figure 18:
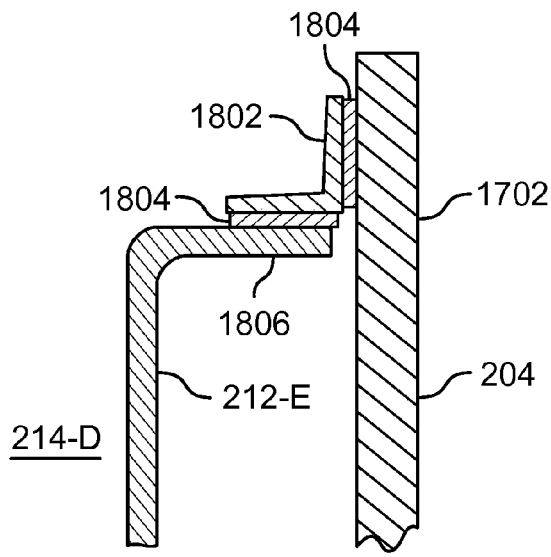
FIG. 18 is a cross-sectional view showing one embodiment of a top seal.

FIG. 18 illustrates a cross-sectional view showing one embodiment of a top seal 1802. The top seal 1802 prevents water or other fluid from entering the space between the insert 212-E and the box 204 and also provides a mechanical connection joining the insert 212-E to the box 204. The insert 212-E fits inside the box 204 with the lip 1806 of the insert 212-E below the top of the box 204. In the illustrated embodiment, the insert 212-E fits loosely inside the box 204 with a small clearance between the lip 1806 of the insert 212-E and the inside of the sidewall 1702. In another embodiment, the insert 212-E fits snugly inside the box 204 with minimal or no clearance.

In order to prevent the intrusion of water or other fluid in the area between the insert 212-E and the box 204, the lip 1806 of the insert 212-E is sealed to the inside surface of the box 204. In the illustrated embodiment, a seal 1802 fits into the corner defined by the upper surface of the lip 1806 and the inside upper surface of the box 204. The seal 1802 has a first member secured to the lip 1806 with an adhesive material 1804, for example, double-sided tape. The seal 1802 has a second member secured to the box 204 with an adhesive material 1804, for example, double-sided tape. In one embodiment, the first and second members of the seal 1802 are connected together with a flexible joint. In one embodiment, the adhesive material 1804 is one piece that extends from the lip 1806 to the inside upper surface of the box 204. In another embodiment, the seal between the insert 212-E and the box 204 is accomplished with a sturdy waterproof tape attached to and joining the lip 1806 and the box 204. In yet another embodiment, the seal between the insert 212-E and the box 204 is accomplished with a material, such as silicone RTV, that is applied as a bead in the corner between the insert 212-E and the box 204.

Figure 21:
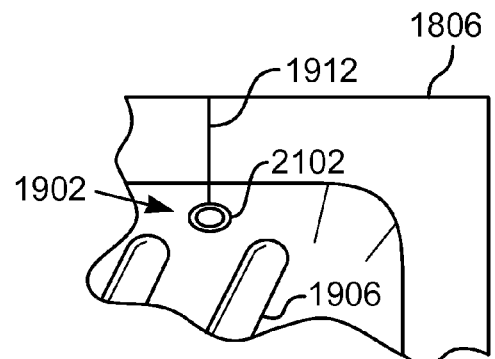
FIG. 21 is a partial top plan view of one embodiment of the cable through-way shown in FIG. 19.
Figure 20:
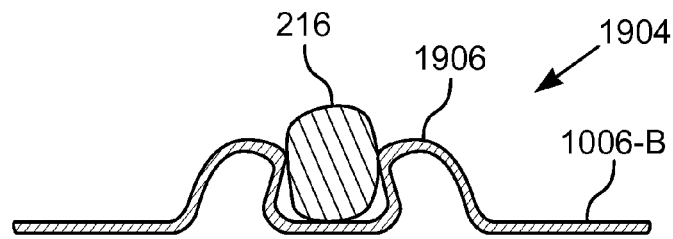
FIG. 20 is a cross-sectional view of one embodiment of the cable support shown in FIG. 19.
Figure 19:
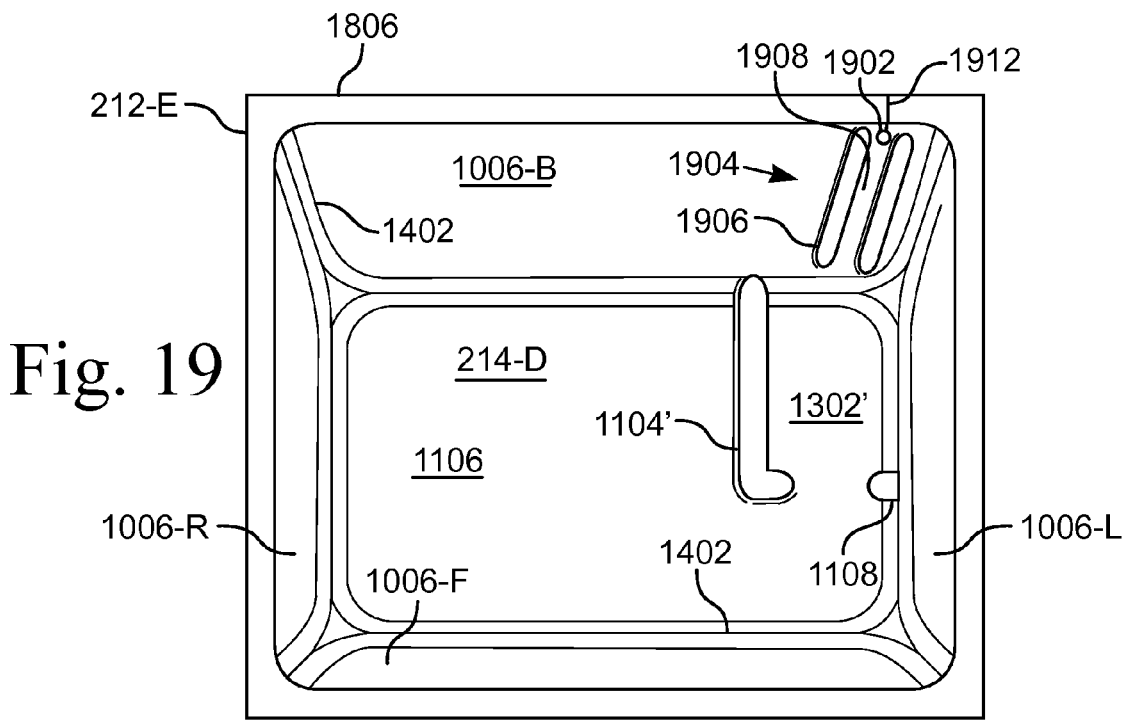
FIG. 19 is a top plan view of the embodiment of the insert shown in FIG. 16.

FIG. 19 illustrates a top plan view of the embodiment of the insert 212-E shown in FIG. 16. In the illustrated embodiment, the insert 212-E has radiused corners 1402 where the four walls 1006-R, 1006-L, 1006-B, 1006-F and the floor 1106 meet. FIG. 20 is a cross-sectional view of one embodiment of the cable support 1902 shown in FIG. 19. FIG. 21 illustrates a partial top plan view of one embodiment of the cable through-way 1902 shown in FIG. 19.

The back wall 1006-B includes a cable support 1904 and a cable through-way 1902. The cable support 1904 is a guide-way for the cable 216 from the pump 312 inside the insert 212-E and the through-way 1902 is a passage from the cavity 214-D to the compartment 318 between the insert 212-E and the box 204. The pump 312 is positioned in the space or recess 1302'. The cable 216 from the pump 312 is secured between the cable grips 1906 and then the cable 216 passes through the through-way 1902 into the compartment 318 behind the back wall 1006-B of the insert 212-E.

The pair of cable grips 1906 are spaced apart with a gap sized to receive the cable 216 therebetween. The pair of cable grips 1906 have a configuration that grips the cable 216. A channel 1908 is formed between the grips 1906 and the channel 1908 has a narrow opening compared to the width at the bottom of the channel 1908. Such a configuration allows the cable 216 to be pressed into the channel 1908 and secured in place with the narrow opening pinching the cable 216 between the outer edges of the channel. The length of the cable grips 1906 is sufficient to secure the cable 216 to the insert 212-E between the pump 312 and the cable through-way 1902. In another such embodiment, each of the cable grips 1906 is a series of protrusions into the cavity 214-D with a configuration to hold the cable 216 captive between the cable grips 1906.

The cable through-way 1902 is a hole in the back wall 1006-B near the top of the cable support 1904. A slit 1912 extends from the rear edge of the ledge 1806, across the ledge 1806, and down the back wall 1006-B to the hole 1902. The material of the insert 212-E is sufficiently flexible and resilient that the slit 1912 can be opened sufficiently such that the cable 216 can be forced between the edges of the slit 1912 and into the hole 1902. The slit 1912 in one embodiment is formed such that the adjacent edges contact each other, thereby preventing intrusion of water into the space between the insert 212-E and the box 204. In another embodiment, the slit 1912 is sealed with a sealant, such as an RTV silicone sealant, to prevent intrusion of water. In yet another embodiment, the slit 1912 is sealed by the top seal 1802. In the embodiment illustrated in FIG. 21 a grommet 2102 is placed in the hole 1902 to protect the cable 216 from the edges of the hole 1902 and to seal the hole 1902 to prevent fluid in the cavity 214-D from entering the space between the insert 212-E and the box 204.

The disposable therapy device 100 includes various functions. The function of controlling the flow of fluid through the pad 302 is implemented, in one embodiment, by the control unit 224 that is operatively connected to the pump 312 to turn the pump 312 on and off based on operation of a manual control and/or by operation of a timer circuit that switches the power to the pump 312.

The function of minimizing thermal transfer between the ambient environment outside the container 102 and the contents of the cavity 214 is implemented, in one embodiment, by the insulated insert 212-A, which is a material with low thermal conductivity, such as Styrofoam. In another embodiment, the function of minimizing thermal transfer is implemented by a shell insert 212-B inside a box 204 with an air gap between the two 212-B, 204. In such an embodiment, the physical connection between the shell insert 212-B and the box 204 is only large enough to provide the necessary structural integrity to support the shell insert 212-B in the box 204. In one such embodiment, the air gap is filled with an insulating material that has a lower thermal transfer rate than air. In yet another embodiment, the function of minimizing thermal transfer is implemented by a molded insert 212-C inside a box 204 with insulation 1102 between the insert 212-C and the box 204.

The function of supplying temperature controlled fluid to a thermal pad 302 is implemented, in one embodiment, by a pump 312. In one embodiment, the pump 312 is submergible and secured to the bottom 508 of a cavity 214 that is filled with a fluid.

The function of providing a therapy device 100 that is disposable is implemented, in one embodiment, by fabricating the device 100 with a minimum of non-biodegradable materials. In one such embodiment, the container 102 and the shell insert 212-B, which make the bulk of the material of the device 100, are biodegradable materials, such as cardboard.

The function of routing a cable 216 from the pump 312 in the cavity 214 to the compartment 318 between the insert 212 and the box 204 is implemented, in one embodiment, by the channel 316 and the notch 304 in the insulated insert 212-A. In another embodiment, the cable 216 is routed through the space between adjacent connectors 504 near the upper inside corner of the box 204. In yet another embodiment, the cable 216 is routed through the cable trough 1004 and into an opening 1110 to the compartment 318.

The function of ensuring that the cavity is waterproof and is capable of holding a quantity of liquid is implemented, in one embodiment, by folding a planar sheet into the basket shape of the shell insert 212-B, with the surface of the shell insert 212-B that defines the cavity 214-B, being waterproof. For example, in various embodiments the planer sheet is waterproof, the surface of the sheet is coated or otherwise treated to make it waterproof, or a waterproof liner is positioned inside the cavity 214 adjacent the surface of the cavity 214.

The function of securing the insert 212 to the box 204 is implemented, in one embodiment, by the insert 212-A having a tight fit in the box. In this way, the planar outer walls of the insert 212-A engage the inside surface of the box 204 to retain the insert 212-A in the box 204. In another embodiment, adhesive is applied to selected portions of the insert 212 where it contacts the box 204 and/or the insulation 1102.

From the foregoing description, it will be recognized by those skilled in the art that a disposable therapy device 100 has been provided. The device 100 is a self-contained therapy device that is fabricated of materials that are readily disposable, but sufficiently strong and durable to survive a course of treatment that may last several months.

While the present invention has been illustrated by description of several embodiments and while the illustrative embodiments have been described in considerable detail, it is not the intention of the applicant to restrict or in any way limit the scope of the appended claims to such detail. Additional advantages and modifications will readily appear to those skilled in the art. The invention in its broader aspects is therefore not limited to the specific details, representative apparatus and methods, and illustrative examples shown and described. Accordingly, departures may be made from such details without departing from the spirit or scope of applicant's general inventive concept.

What is claimed is:

1. An apparatus for providing thermal therapy to a patient, said apparatus having a shipping configuration and an operable configuration, said apparatus comprising:
   a container having a box and a lid, said lid being releasably securable to close an opening in said box;
   an insert defining a cavity, said cavity being waterproof and configured to contain a quantity of liquid, said insert inside said box;
   a compartment between an inside surface of said box and an outside surface of said insert, said box configured to have an access opening to said compartment;
   a pump having an outlet port and an inlet port, said pump positioned inside said cavity, said inlet port positioned to receive a fluid in said cavity;
   a cable electrically connected to said pump, said cable configured to provide electrical power to operate said pump, said cable routed from said pump to said compartment by passing over a lip of said insert and between said insert and said box, a distal end of said cable stored in said compartment when said apparatus is in said shipping configuration; and
   a pair of conduits configured to connect to a thermal pad, a first one of said pair of conduits connected to said outlet port of said pump, a second one of said pair of conduits having a discharge in said cavity.

2. The apparatus of claim 1 wherein said pair of conduits are stored in said cavity when said apparatus is in said shipping configuration.

3. The apparatus of claim 1 further including a thermal pad connected to said pair of conduits; said thermal pad and said pair of conduits stored in said cavity when said apparatus is in said shipping configuration.

4. The apparatus of claim 1 wherein said container in said shipping configuration has said lid closed with said cable and said pair of conduits enclosed in said container, wherein said shipping configuration is suitable for shipping said apparatus as a self-contained unit without requiring said container to be inserted into another container for protection.

5. The apparatus of claim 1 wherein said container in said operable configuration has said lid closed with each one of said pair of conduits having an end inside said cavity and a distal end outside said cavity, said pair of conduits passing between said lid and said box when in said operable configuration, and said lid accommodating said pair of conduits without restricting a flow of fluid through said pair of conduits.

6. The apparatus of claim 1 further including an insulating material positioned between said cavity and said box.

7. The apparatus of claim 1 further including an insulating material positioned between said insert and said box, wherein said insert is a rigid material defining said cavity, and said insulating material is a plurality of thermal insulation panels.

8. The apparatus of claim 1 further including a passageway in said insert, said passageway receives said cable between said pump and said compartment.

9. The apparatus of claim 1 further including a cable support inside said cavity proximate a sidewall of said insert, said cable support configured to receive and secure a cable from said pump to said sidewall of said insert.

10. An apparatus for a thermal therapy device, said apparatus comprising:
    a container having a plurality of planar panels defining a lid and a box, said lid being releasably securable to said box;
    a plurality of insulation panels positioned proximate an inside surface of said box; and
    an insert defining a cavity, said insert inside said box with said plurality of insulation panels positioned between said box and said insert, said insert and a wall of said box defining a compartment therebetween, said box configured to have an opening communicating with said compartment, said cavity being water proof and configured to contain a quantity of liquid, said insert having a lip that is sealed to an inside surface of said box;
    a pump mounted inside said cavity; and
    a cable electrically connected to said pump for powering said pump, said cable routed from said pump through a passageway formed in a sidewall of said insert where said cable is routed proximate an upper edge of said insert and then passes into a space between said insert and said box.

11. The apparatus of claim 10 wherein said insert has a bottom with at least one protrusion defining a space dimensioned to receive said pump inside said cavity.

12. The apparatus of claim 10 further including a seal between said lip and said inside surface of said box, said seal secured to said lip, and said seal secured to said inside surface.

13. The apparatus of claim 10 wherein said insert includes an opening dimensioned and configured to receive a pair of conduits for connecting to a thermal pad, said opening positioned between said lid and said box.

14. The apparatus of claim 10 further including a cable support inside said cavity, said cable support configured to receive and secure a said cable from said pump.

15. The apparatus of claim 10 further including a handle including a strap, said strap being flexible, a first end of said strap secured between two panels that define the outer surfaces of a sidewall of said box.

16. An apparatus for providing thermal therapy to a patient in a compact single use configuration, said apparatus having a shipping configuration and an operable configuration, said apparatus comprising:
    a box having an inside surface, a top opening, and a side opening;
    a lid having a first edge attached to said box, said lid releasably securable to said box to define a closed configuration;
    an insert defining a cavity, said insert having a ledge surrounding an upper edge, said ledge sealed to an inside surface of said box with a water resistant connection;
    an insulator between said insert and said inside surface of said box;
    a pump having an outlet port and an inlet port, said pump positioned inside said cavity, said inlet port positioned to receive a fluid in said cavity, said pump having a cable for powering said pump, said cable routed through a passage in said insert; and a compartment defined between said insert and said box, said compartment dimensioned and configured to receive a portion of said cable distal to said pump, said side opening in said box positioned to provide access to said compartment whereby said cable is extendable through said side opening.

17. The apparatus of claim 16 further including a handle including a strap, said strap being flexible, a first end of said strap secured between two panels that define the outer surfaces of a sidewall of said box, a joint defined by the box and lid in the closed configuration, said joint having a strap passage configured and dimensioned to allow said strap to extend outside said box with said box and said lid in said closed configuration.

18. The apparatus of claim 16 further including a pair of conduits configured to connect to a thermal pad, a first one of said pair of conduits connected to said outlet port of said pump, a second one of said pair of conduits having a discharge into said cavity, a joint defined by the box and lid in the closed configuration, said joint having a conduit passageway configured and dimensioned to allow said pair of conduits to extend from said cavity to outside said box with said box and said lid in said closed configuration.

19. The apparatus of claim 16 further including a cable support inside said cavity proximate said passage for said cable, said cable support configured to receive and secure a cable from said pump, said cable support including a pair of spaced apart grips defining a channel therebetween, said channel having a configuration with a narrow opening such that a section of said cable is secured in said narrow opening.

20. The apparatus of claim 16 further including a seal having a first member proximate said ledge and a second member proximate said inside surface of said box, said first member attached to said ledge defining a first waterproof connection, said second member attached to said inside surface of said box defining a second waterproof connection.

* * * * *